United States Patent [19]

Miller

[11] Patent Number: 5,295,945
[45] Date of Patent: Mar. 22, 1994

[54] GARMENT AND METHOD FOR POSITIONING AND SECURING A RADIOACTIVE IMPLANT INTERNALLY WITHIN THE FEMALE GENITAL ORGANS

[75] Inventor: Donna M. Miller, Watertown, Mass.

[73] Assignee: Beth Israel Hospital Assoc. Inc., Boston, Mass.

[21] Appl. No.: 923,520

[22] Filed: Aug. 3, 1992

[51] Int. Cl.⁵ .............................. A61N 5/00
[52] U.S. Cl. ........................... 600/6; 2/406; 2/408
[58] Field of Search .......... 604/347, 349; 2/400, 2/401, 406, 408, 243 R; 600/6, 3; 128/845, 898

[56] References Cited

U.S. PATENT DOCUMENTS

| | | | |
|---|---|---|---|
| 1,687,717 | 10/1928 | Epstein | 604/349 |
| 2,484,356 | 10/1949 | Ribeiro et al. | 604/347 |
| 2,719,976 | 10/1955 | Sussman | 2/408 |
| 2,796,865 | 6/1957 | Reinhardt | 604/347 |
| 3,029,814 | 4/1962 | Kravitz | 2/406 |
| 3,060,924 | 10/1962 | Rush | 600/6 |
| 3,613,686 | 10/1971 | De Woskin | 2/406 |
| 3,872,856 | 3/1975 | Clayton | 600/6 |
| 3,974,836 | 8/1976 | Carlson | 2/408 |
| 4,554,909 | 11/1985 | Pino y Torres | 600/6 |
| 4,597,110 | 7/1986 | Smith, Jr. et al. | 2/406 |
| 4,637,078 | 1/1987 | Southwell | 2/408 |
| 4,675,918 | 6/1987 | O'Brien | 2/402 |
| 4,802,469 | 2/1989 | Gollestani | 2/408 |
| 4,835,795 | 6/1989 | Lonon | 2/408 |
| 5,086,519 | 2/1992 | Rokasky | 2/406 |
| 5,131,386 | 7/1992 | Simmons | 2/401 |

FOREIGN PATENT DOCUMENTS

| | | | |
|---|---|---|---|
| 562013 | 5/1975 | Switzerland | 2/400 |
| 1256183 | 12/1971 | United Kingdom | 2/406 |
| 2195230 | 4/1988 | United Kingdom | 2/400 |

Primary Examiner—Clifford D. Crowder
Assistant Examiner—Amy B. Vanatta
Attorney, Agent, or Firm—David Prashker

[57] ABSTRACT

The present invention provides a garment to be worn externally on the female person and a method for positioning and securing a radiotherapeutic appliance internally within the female genital organs during local radiation therapy. The garment provides at least one supporting band of material to be worn around the female body and provides access on-demand to the vulva of the person. The garment also provides at least one extensible member for positioning and securing the radiotherapeutic appliance such that the appliance is maintained in position and secured against movement during the radiation therapy.

6 Claims, 13 Drawing Sheets

GARMENT AND METHOD FOR POSITIONING AND SECURING A RADIOACTIVE IMPLANT INTERNALLY WITHIN THE FEMALE GENITAL ORGANS

FIELD OF THE INVENTION

The present invention is concerned with radiation therapy for gynecologic cancers; and is particularly directed to intracavitary devices containing radioactive materials employed commonly in local irradiation of gynecologic cancer patients.

BACKGROUND OF THE INVENTION

Radiation therapy involves the use of high-energy x-rays or ionizing radiation in the treatment of malignant neoplasms and occasionally in the treatment of certain benign conditions. Depending on the type of cancer, its stage of development, its spread, and its location within the body, radiation therapy may be used as the primary curative treatment for cancer; or as an adjunctive treatment to surgery; and/or chemotherapy. The radiant energy employed during radiation therapy is thought to produce biologic change by damaging the DNA molecule of target tissues and thus hampering further effective replication of those tissues and cells. A common misconception is that therapeutic radiation severely affects malignant cells while sparing normal tissues. In actuality, the critical difference in the effect of radiation on various tissues is the ability of the normal cells and tissues to recover from radiation damage.

Two forms of radiation therapy are conventionally known: external radiation therapy (teletherapy) and internal radiation therapy (brachytherapy). External radiation therapy is administered using x-ray, gamma-ray, or electron-producing machines. Internal radiation therapy involves the insertion of radioactive isotopes directly into tumors or the tissues surrounding tumors to produce a local concentration of radiation often using appliances such as the vaginal cylinder radiation implant. The major advantage of local irradiation is that a relatively high dose of ionizing radiation can be applied to a limited anatomical area or region with accuracy and precision while protecting other tissues from potential harmful effects. Note, however, that a basic principle of radiation therapy states that the intensity of radiation is inversely proportional to the square of the distance from the radiation source (inverse square long). Thus, the proper positioning of the radioactive implant or appliance internally is of utmost importance.

The treatment of cervical cancer, uterine cancer, and vaginal cancer in the female patient are often considered as the prime examples of a successful combination of internal and external radiotherapy. External radiation therapy is usually used initially to diminish the volume of the central tumor or tumor bed area. Then, an additional dose of radiation is delivered to the tumor or designated area at greatest risk for recurrence using intracavitary or interstitial radiation devices and implants. Intracavitary implants include the vaginal cylinder radiation implant, and the tandem and colpostats. Interstitial vaginal implants include the "MUPIT" or Martinez Universal Perineal Interstitial Tool. The tandem and colpostats and MUPIT implants are inserted in the operating room under anesthesia; and are secured by suturing the labia closed or by suturing the appliance to the body.

It is estimated today that approximately 300 radioactive implant procedures are performed each year within hospitals in the greater metropolitan Boston area. All of the currently employed protocols for positioning and securing a vaginal cylinder radiation implant containing radioactive materials are makeshift and haphazard. Some hospitals rely heavily on the use of adhesive tape to immobilize the implant with the invariable consequence that the patient suffers major skin irritations and skin burning. One institution typically employs trache tape while others use adhesive tapes of various kinds. Alternatively it should be noted and appreciated also that one hospital routinely sutures the labia together to secure the implant after it has been inserted internally into the vagina. This is presently considered the most drastic and draconian procedure used today for securing a radiation implant internally.

It is useful here to briefly describe a current procedure for using a vaginal cylinder radiation implant which is to be positioned within the vagina for radiotherapy of either the vaginal wall or the cervix. The vaginal cylinder radiation implant is used most often for patients with early stage endometrial (uterine) cancer and is used less frequently for patients with cervical or vaginal cancer. These women are usually fairly healthy aside from their diagnosis of early stage localized cancer; and many have had a total abdominal hysterectomy prior to beginning the course of radiation therapy. The cylindrical implant is usually used following 5-6 weeks of daily external radiation treatments to the pelvis. The implant delivers an additional concentrated dose of radiation to the area at highest risk of recurrence of tumor while reducing the risk of bowel complications.

About two weeks after completing the external radiation treatments, the patient comes in to the hospital for an implant teaching session and pre-admission testing. The radiation oncology nurse teaches the patient about the upcoming implant procedure and gives the patient a tour of the hospital room where she will be confined during her stay.

The evening before her hospital admission, the patient begins a prepatory bowel cleanout. On admission to the hospital, a nurse completes the cleanout and inserts a foley catheter into the patient's bladder; the patient is then ready for the vaginal implant. Accompanied by the radiation oncology nurse, the physician inserts the pre-lubricated vaginal cylinder implant into the patient's vagina while the patient is lying in bed. The handle at the end of the cylinder protrudes externally from the vagina for approximately two inches after insertion. The current practice involves packing the vagina with gauze to keep the implant from moving. The outside skin around the vagina is then covered with gauze and is typically taped with elastoplast and adhesive to secure the implant. This tape is brought up to the abdomen anteriorly and the buttocks posteriorly to provide adequate support. Once the implant is taped in place, the radiation nurse and the physician leave the room, with the patient lying in bed.

Due to the radioactivity, the door to the patient's room is kept closed and visits are limited. Nurses can visit up to 30 minutes per 8 hour shift. Other visitors are limited to 30 minutes per person per day. No pregnant women or children under 18 are allowed in the room. The patient does have access to television and telephone, and books, knitting, or other diversionary things she has brought with her to occupy herself.

During the treatment, the patient must remain in bed, on her back or on her side, with her legs relatively straight. She is maintained on a clear liquid diet; has a urinary catheter in place; and is placed on anti-diarrheal medications to prevent her from having a bowel movement during the implant stay. Medications are provided if needed for anxiety and pain. Although the treatment is not considered very painful, it is often uncomfortable and many patients also experience feelings of significant isolation.

Even with the minimal movements that a patient makes lying in bed, the tape holding the implant often curls and bunches, a condition which causes skin irritation and discomfort. The nurse is limited in what she can do with the tape because the implant may become dislodged if the tape is manipulated. She may trim the end of the tape as much as is possible without jeopardizing the security of the implant; this may mitigate the discomfort but usually does not eliminate it.

Regardless of the difficulties and discomfort, it is critical that the implant remain immobilized and lodged at the chosen site. Tape has been used conventionally simply because it is freely available; however, tape takes time to put on and it presents discomfort and pain unrelated to the actual treatment for the cancer. Adjusting the tape may decrease the patient's discomfort but certainly reduces the nurse's quality time available for that patient.

After the prescribed number of radiation hours, the implant must be removed by the physician. The tape is removed first and then the implant is taken out. Removal of the implant itself is usually not painful; however, the taped area of the skin is often reddened and sore since the outer layer of skin may be taken off when the tape is removed. The irritation caused by this process may last up to two weeks, so the patient may continue to feel discomfort simply due to the means of securing the implant.

Clearly, there is a well recognized and long-standing need for alternatives and improvements in the means for securing and immobilizing a radiotherapeutic device or implant internally within the vagina. The use of tape causes skin irritation and tape burns; increases the discomfort for the patient; may cause radiation exposure to staff nurses who attempt to make the tape more comfortable for the patient; and places unnecessary demands of the attending nursing staff. Note, however, that the only presently available alternative is the suturing of the labia with the concomitant increased risk of infection and the major increase of patient discomfort. Accordingly, a garment which can be worn externally on the body and which is able to position and secure a radiotherapeutic appliance internally within the vagina would be generally recognized as a major achievement and beneficial advance in this area by both oncologists and nurses alike.

SUMMARY OF THE INVENTION

The present invention provides a garment to be worn externally on the female person for positioning and securing a radiotherapeutic appliance internally within the female genital organs during local radiation therapy, said garment comprising:

at least one supporting band of material having anterior and posterior aspects to be worn around the torso of the female body, said supporting band providing access on-demand to the vulva of the person;

at least one member for positioning and securing the radiotherapeutic appliance, said member being comprised of (1) a first end joinable to said posterior aspect of said supporting band, (2) a body extensible substantially about the medial plane of the female person to overlay the vulva at least in part, said body being extended after a radiotherapeutic appliance has been inserted internally into the female genital organs for radiation therapy, (3) a second end attachable to and detachable from said anterior aspect of said supporting band on-demand, and (4) means for securing the position of the inserted radiotherapeutic appliance internally within the female genital organs.

BRIEF DESCRIPTION OF THE FIGURES

The present invention may be more easily and completely understood when taken in conjunction with the accompanying drawing, in which.

DETAILED DESCRIPTION OF THE PRESENT INVENTION

Figure 1:
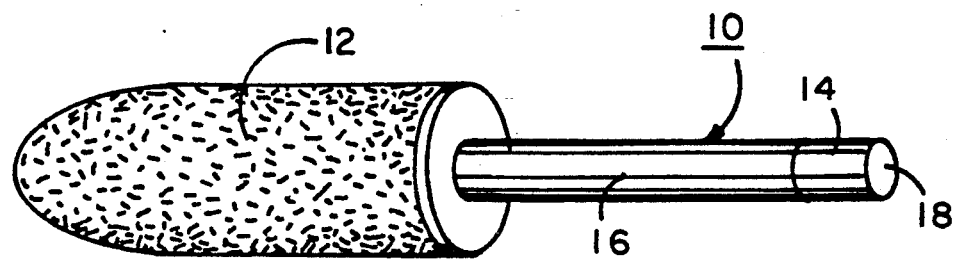
FIG. 1 is a perspective view of one type of radiation implant conventionally employed for local radiation therapy.

The present invention is a garment, an article of manufacture, to be worn externally on the female body and person in order to position and secure a radiotherapeutic appliance internally within the female genital organs during local radiation therapy. By its construction and structure, the garment provides a band of material which is to be worn around the torso of the female body, preferably around the waist and/or hip area; provides at least one member which extends substantially about the medial plane of the female person; and, after the radiotherapeutic appliance has been internally inserted, is placed to overlay the vulva at least in part for maintaining the position of the inserted appliance. Optionally, the member also exerts a compression force upon the inserted appliance to secure it further internally within the female genital organs. The present invention thus provides a variety of major advantages and benefits to the user. These include the following:

1. The garment is to be positioned around the torso of the female body before either the radiotherapeutic appliance or the urinary catheter is inserted by the physician. The extensible member or members are detached from the anterior aspect of the supporting band thereby allowing the physician and attending oncology nurse an unobstructed and unhindered access to the vulva. A radiotherapeutic appliance such as the vaginal cylinder radiation implant is inserted at the prechosen area requiring local radiation. The physician typically packs the vagina with gauze to maintain a desired spacing internally such that the radioisotope lies adjacent to the tumor cells. The member or members comprising the garment are then extended about the medial plane of the female person to overlay the vulva at least in part; and, by this manipulation and the attachment of the member to the anterior aspect of the supporting band of the garment, the inserted radiotherapeutic appliance lies properly positioned and secured at the chosen site within the female genital organs.

2. The present invention permits the physician and/or oncology nurse attending the patient to check the positioning of the internalized radiotherapeutic appliance periodically when necessary. The positioning and securing member(s) of the present invention may be detached from the anterior aspect of the supporting band immediately, at will, and as necessary—one one or more occasions. The physician or nurse then is able to rectify the position of the radioisotope or make such other corrections and adjustments as are deemed necessary for the therapeutic benefit and comfort of the patient. The member(s) of the garment are then extended once more around the medial plane of the female body to again overlay the vulva; and are again attached to the anterior aspect of the supporting band comprising the present invention. In this manner, one or more adjustments to the location of the internalized radiotherapeutic appliance may be made at any time with limited inconvenience or discomfort to both the patient and the attending physician.

3. The present invention is a garment which is comfortable to the patient undergoing local radiation therapy and yet maintains a firm positioning and securement of the internalized radiotherapeutic appliance within the female vagina. The present invention avoids and eliminates skin chafing, skin irritations, and skin burning. Similarly, the garment eliminates any need for suturing the labia or other surgical procedure in order to secure the appliance internally.

4. While various embodiments of the present invention are expected to be manufactured to accommodate one or the other of these various appliance formats, it is expected and intended that each form of radiotherapeutic appliance will have a particular style of garment which is intended for use with only one form of implant. Given the range and variety of embodiments envisioned by the present invention, any conventionally known radiotherapeutic appliance may be accommodated and employed with ease and convenience.

The subject matter as a whole which is the present invention broadly encompasses a variety of different constructions and structures; provides a variety of distinctive formats; and permits the user to employ various modes of usage to accommodate the diverse range of radiotherapeutic appliances conventionally known. To insure a thorough comprehension and complete understanding of the essential components as well as the optional desirable features permitted within the various embodiments of the present invention, the detailed description will be presented in the following sequence: a detailed disclosure of the major and essential component parts of the garment; a description of various preferred embodiments of the present invention with and without optional features; and a delineation of useful but less preferred alternative embodiments of the present invention.

I. Component Parts of the Present Invention

The garment for positioning and securing a radiotherapeutic appliance internally within the female genital organs during local radiation therapy comprises only two essential component parts: at least one supporting band of material having anterior and posterior aspects; and at least one member for positioning and securing the radiotherapeutic appliance after insertion internally. Each essential component part will be described individually.

A. The Supporting Band

The supporting band is desirably composed of flexible or supportive material; and is to be worn around the torso of the female body, preferably around the waist and/or hips. The supporting band encircles the torso and has anterior and posterior aspects--which in certain embodiments may be arbitrarily designated after the supporting band is suitably positioned around the body. It is most desirable that the supporting band be composed of an elastomeric fiber such that the band tightly encircles the torso and supports the abdomen and hips.

The band material is also desirably biocompatible with the skin; and may be of a woven or non-woven nature to provide a soft nap and finish for the textile fabric. In addition, because the garment is intended to be used on one occasion only in almost all instances, it is of little or no importance whether the fibers employed to make the textile comprising the supporting band be long-lasting, or of short duration strength, or intended for a single one time use.

The purpose and goal of the supporting band, regardless of configuration or dimensions, is as a stationary cincture or girdle which is positioned around the torso of the female body and which serves as the supporting surface and structural basis from which the single member or multiple members may be extended for proper use. In each embodiment of the supporting band, it is necessary and essential that the vulva remain accessible by the physician and/or attending nurse after the supporting band has been located around the torso. Such access to the vulva of the female person need exist only on-demand; or, alternatively, such access may be continuous and constant throughout the time the supporting band is worn by the female person. Given this essential criteria for the supporting band in each embodiment of the present invention, it is expected and envisioned that the supporting band will take form in at least the following formats:

1. As a waistband, sash, or cord: This format employs narrow constructions of supporting bands which will range in size from a drawstring width to a waist and hip encircling girdle which is typically 6-18 inches in width. This sash or girdle format typically will not extend in width below the abdomen or hips of the body, thereby leaving the thighs and crotch area of the human body uncovered and exposed to view. All such sashes, girdles, and cords, regardless of shape and dimensions, are suitable for use as a supporting band.

2. A split-crotch or crotchless panty: The split-crotch or crotchless panty is a most preferred format of the supporting band. The panty material itself is desirably a flexible elastomer and may be configured as bikini briefs, abdomen and buttock covering panties, or a long, full-length panty which extends in width from the hip to the waist. The panty itself may be a single layer of material or be a multi-layer laminate textile in accordance with the wishes or needs of the intended user. On-demand access to the vulva of the female is provided as a structural feature of the panty in a number of alternative ways. an elongated slit in the crotch area of the panty is suitable as one means of access on-demand--but it is desirable that such a slit be reinforced at its edges and extend in length for a distance of at least two-three inches. Alternatively, the crotch fabric area may be split entirely, thereby exposing the labia to view while covering the inner thigh area around each leg of the person. This format provides on-demand access to the vulva and yet provides a cloth covering and protection for the female surrounding her legs and thighs immediately adjacent to the vulva itself. Finally, the entire crotch area fabric may be omitted or deleted entirely to form a crotchless panty. This format provides only enough material to encircle the legs and thighs of the female body while exposing the entirety of the mound pubis as well as the vulva itself. The variations of format and design construction features within the panty style of supporting band is solely the choice of the female patient and/or the attending physician or nurse. Many persons feel far more comfortable and at ease wearing some kind of fully constructed panty as underwear; and it is both valuable and desirable to provide the patient with as much comfort and ease as possible considering the intended use circumstances. Accordingly, any panty style garment which provides on-demand access to the vulva is suitable for use as a supporting band.

Figure 26:
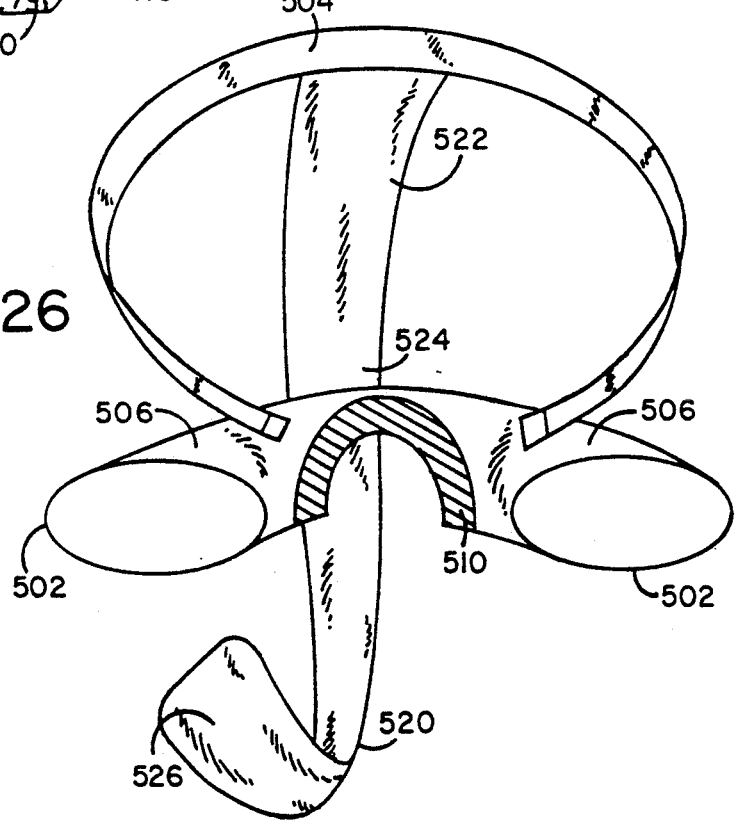
FIG. 26 is a perspective view of a second alternative embodiment of the present invention.

3. A thigh loop and waistband article of manufacture. This type of construction is regarded as generally less desirable for most use occasions, but is recognized as needed under very specific circumstances. A waistband loop surrounds the waist and/or hips of the person; similarly, individual loops of elastomeric material are placed upon each thigh of the female patient. A central cloth panel joins the waistband loop to each of the thigh loops and covers the abdomen of the female body primarily. On-demand access to the vulva is provided through the central cloth panel which is positioned effectively along the median plane of the body. An illustrative example of this format is shown by FIG. 26.

B. The Single Member or Plurality of Members.

It is required that at least one member or ribbon of material exist as a component part of the garment comprising the present invention. While one individual member or a plurality of different members may be present, it is required that at least one member be employed for positioning and/or securing the radiotherapeutic appliance after it has been inserted internally within the female genital organ. Each member present, regardless of whether it be as a single strip of material or as a plurality of different ribbons of material, is individually comprised of:

1. a first end joined permanently or temporarily to the posterior aspect of the supporting band;

2. a flexible or inflexible member body extensible substantially around the medial plane of the female person to overlay the vulva at least in part after a radiotherapeutic appliance has been inserted internally into the female genital organ; and 3. a second end attachable to and detachable from the anterior aspect of the supporting band on-demand.

In addition, two other structural features and requirements are desirably provided by the member or members comprising the garment. If a single member is present in that embodiment of the garment, both of the structural features are preferably present and provided by the single member alone. Conversely, if a plurality of members are present in that particular embodiment of the garment, each structural feature maybe provided by a different member individually. In this manner, both the location and the particular structural means will vary markedly with the numerical quantity of members which are present in that embodiment. These structural features are:

4. appliance engaging means for maintaining the position of the inserted radiotherapeutic appliance internally within the female genital organ after it has been located at a prechosen site by the physician; and 5. optionally, force generating means for exerting a limited compression force upon the radiotherapeutic appliance in order to secure the appliance internally within the female genital organs after it has been inserted and located at a prechosen site by the attending physician.

It is useful to recognize and appreciate the purpose and function of the single member (or the plurality of different members) as a structural component of the present invention. The overall goal for the member is the proper positioning and firm securing of the radiotherapeutic appliance after it has been inserted internally into the female genital organs for radiation therapy. It is crucial to remember that the radioisotope is to be located and positioned adjacent the cancerous tumor in order that local radiation therapy be effective. Moreover, because the cancerous tumor cells may be located in the uterus, the cervix, or the vagina, it is thus necessary that the physician first place the radiotherapeutic appliance at the proper location. Moreover, because the variety of conventionally known radiotherapeutic appliances is large and diverse even among radioactive implants, different styles and constructions are often favored and employed among physicians. Thus, some favored radioisotope implants are pre-loaded while others are desirably after-loaded. Merely representative of the range and varieties for these conventionally known implant structures are those illustrated by FIGS. 1-3 respectively.

The implant illustrated by FIG. 1 reveals an implant 10 having a substantially dome shaped head 12 containing the radioisotope of choice, a removable cap 14, an extended rod-shaped shaft 16 and a shaft end 18. This radioactive implant 10 is typically positioned adjacent to the cervix or the vaginal cervical tissues for local radiation therapy.

Figure 2:
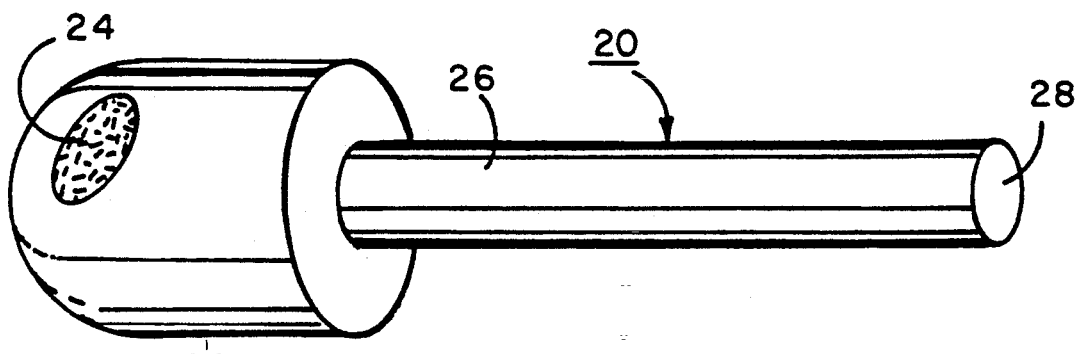
FIG. 2 is a perspective view of another type of radiation implant conventionally employed.

In comparison, a cylindrical implant 20 is shown by FIG. 2 having a bulbus-shaped head 22, a substantially spherical radioisotope section 24 within the head 22, an extended flattened, stick-like body 26, and an end 28. This type of implant is typically employed to position a radioisotope against a portion of the cervical or vaginal tissues for local radiation therapy purposes. Note that the bulbus-shaped head 22 is intended to be inserted into the vagina and to abut the cervical area itself. This allows the radioisotope section 24 to be aligned and lie adjacent to the tumor tissues lying adjacent to the vagina. The end 28 of the stick-like body 26 will extend externally from the vagina and becomes surrounded by the labia after the cylindrical implant 20 has been properly positioned by the physician.

Figure 3:
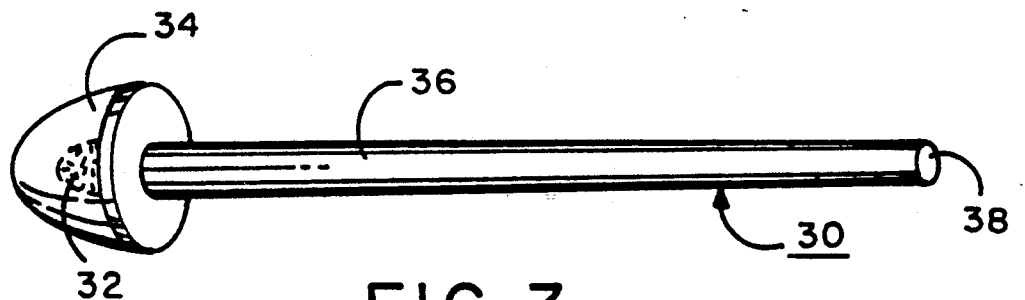
FIG. 3 is a perspective view of a third type of radiation implant conventionally employed.

An alternative construction of vaginal implant 30 is illustrated by FIG. 3. As shown therein, the vaginal implant 30 has a radioactive extended tip 32 which is intended to lie adjacent to the tumor cells in the vagina. The body section 34 of the implant will fill the vaginal cavity at least partially; and the rod-shaped tail 36 and end 38 will extend from the vagina externally.

It is important to note that the various implant structures illustrated by FIGS. 1-3 respectively, after being inserted into the vaginal canal by the physician, must be secured; and, in particular, that the end portion of each implant be immobilized as it extends externally from the vagina and labia. It is this securing and immobilizing function which is the purpose and goal of the present invention.

To achieve this goal and purpose, the single member (or the plurality of members) comprising each embodiment of the garment is fixed temporarily or permanently at one end to the posterior aspect of the supporting band; and is also attachable to and detachable from the anterior aspect of the supporting band on demand and on repeated occasions. The flexible or inflexible body portion of each member thus is intended to extend around the buttocks of the body substantially about the medial plane of the person; and is brought forward anteriorally to overlay the vulva at least in part. The single member or the plurality of different members provides engaging means for maintaining the position of the inserted radiotherapeutic appliance internally by engaging the end of the appliance which extends externally from the vagina. Optionally, the single member of the plurality of members also exerts a limited compression force on the end of the implant extending externally; and thereby secures the appliance in the intended position in a reliable and durable manner. It is the second end of the member or members which are attachable to and detachable from the anterior aspect of the supporting band on demand; and, by attaching the member end(s) to the anterior aspect of the supporting band, both the appliance engaging means and the optional force generating means become effectively employed.

It will be noted that one or more conventionally known closures are intended to be employed as the means by which the second end of each member becomes attachable to and detachable from the anterior aspect of the supporting band at will and on demand, repeatedly. A variety of different styles of closure and closure materials are available; and the user has the choice of employing any one or more of these different closure styles and mechanisms in order that on-demand attachment and detachment of the members occur at will. The closures may be positioned at various prechosen locations on the surface of each member and/or the supporting band; and the physician or attending nurse may use any one or more of the provided closures as he sees fit. The closures also provide the capability to position and reposition the externalized portion of the radiotherapeutic appliance along any or all of the X, Y, and/or Z axes; and each member may be positioned and repositioned repeatedly to engage the externalized portion of the implant in order that the required correct positioning be maintained internally within the female genital organ and that the radioisotope portion of the implant lie adjacent to the tumor tissue. The closures also provide the capability to achieve a tighter or looser fit for the individual and, if desired, to generate a lesser or greater compression force upon the externalized tail portion of the radiotherapeutic appliance in order that the securing of the implant or appliance be firm and reliable.

A broad and diverse range of different closure materials, closure styles, and closure constructions may therefore be employed with the present invention. Most preferred are conventional VELCRO fasteners and strips positioned at multiple locations on both the supporting band and each of the members individually. In addition, other representative closure styles and constructions include snaps, hook and eye connectors, buttons, string ties, and even zippers. All of the above represent durable and long-lasting forms of closures; and all of them are conventionally known and commercially available in many models, sizes, and materials.

In some embodiments, however, a less enduring closure construction may be desirable, especially considering that the garment is generally to be employed in a single one-time use. Representative examples of non-durable closures suitable for use with the present invention include adhesives in patch form; removable solid clips and fasteners; and even pins of various kinds. These latter examples are generally not permanent features and attachments to the fabric; and may be removed and/or lost as a result. These latter examples, therefore, constitute the least desirable forms of closures which may be usefully employed with the present invention. Accordingly, it will be recognized and understood generally that any form of conventionally known closure may be employed with the present invention regardless of its construction, material, or mode of use—so long as it can provide a means of attachment to and detachment from the anterior aspect of the supporting band on-demand.

II. Different Preferred Embodiments of the Present Invention

Three different preferred embodiments are described below. Each is individually useful and desirable under specific circumstances; and none of the preferred embodiments is deemed to be more desireable over another. As will be disclosed, however, each preferred embodiment provides particular features and variations in the degree of control for positioning and securing the externalized end of a radiotherapeutic appliance after it has been inserted internally into the female genital organs for local radiation therapy.

A. The First Preferred Embodiment

Figure 4:
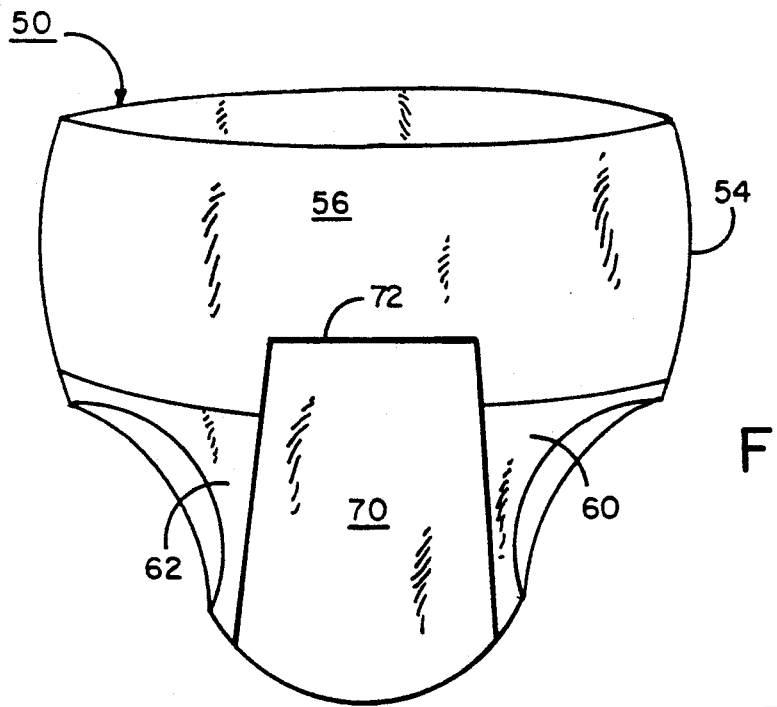
FIG. 4 is a rearward view of a first preferred embodiment of the present invention.
Figure 5:
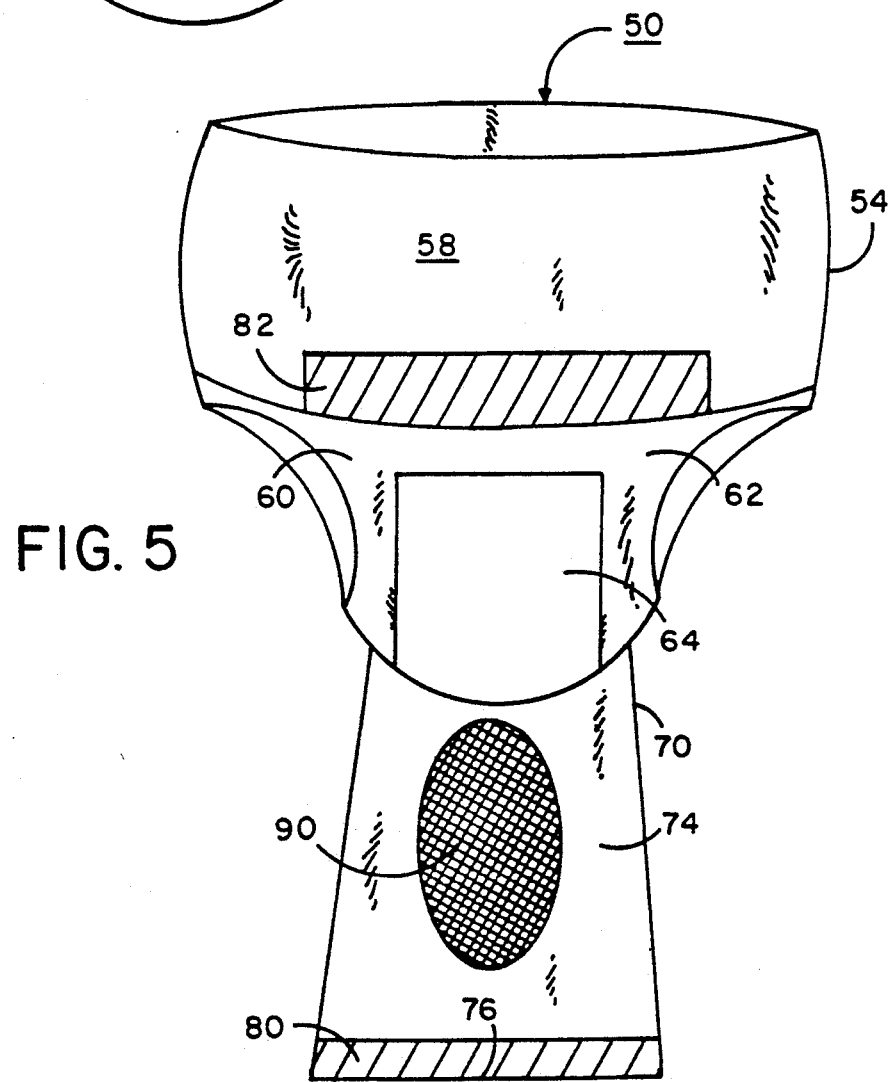
FIG. 5 is a forward view of the first preferred embodiment of FIG. 4.
Figure 6:
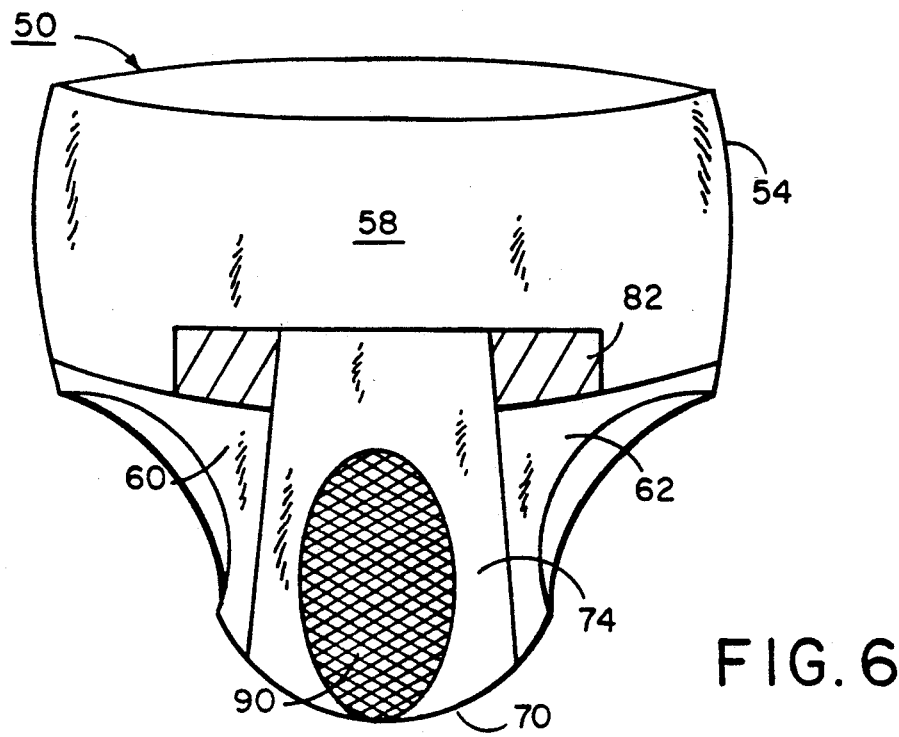
FIG. 6 is a forward view of the first preferred embodiment of FIGS. 4 and 5 in fully deployed form.

The first preferred embodiment is illustrated by FIGS. 4-6 respectively and reveals a panty style of garment which is to be worn around the torso of the female body as underpants. A rear view of the garment is illustrated by FIG. 4; and frontal views of the garment are provided by FIGS. 5 and 6 respectively.

This first preferred embodiment 50 illustrates a supporting band formed as a crotchless panty which comprises an encircling girdle 54 having a rear aspect 56 and a front aspect 58, leg and thigh sections 60, 62, and a rectangular-shaped aperture 64 in the crotch area. A single member 70 has a first end 72 joined to the posterior aspect of rear section 56, a flexible body 74, and a second end 76 which is detachable to and detachable from the anterior aspect 58 of the encircling girdle 54. Along the second end 76 is disposed a VELCRO strip 80 which will interact with another aligned velcro strip 82 positioned centrally on the anterior aspect 58 of the encircling girdle 54 comprising the supporting band. VELCRO strips 80, 82 will act in combination to provide closure means for the single member 70; and allows the user to attach and detach the member repeatedly from the surface of the crotchless panty.

In addition, a highly desirable but entirely optional friction zone 90 is situated within the flexible body 74 proximal to the second end 76. The friction zone 90 is specifically prepositioned such that when the second end 76 is attached via VELCRO strips 80, 82 to the encircling girdle 54 comprising the crotchless panty, the friction zone 90 substantially overlays and encompasses the rectangular shaped aperture 64 as illustrated by FIG. 6. The friction zone 90 may be constructed as an integral portion of the member body 74; or be attached (by sewing or by use of adhesives) to the fabric of the single member 70 to form a laminate composition over that portion of the flexible body 74.

The friction zone 90 is most desirable for direct engagement with the externalized end of the radiotherapeutic appliance after it has been inserted internally into the female genital organ. The non-slip surface and high friction area provided within the friction zone 90 engages and secures the externalized end and holds the implant in the intended location relative to the tumor. It will be noted and appreciated also that the single member 70 and the friction zone 90 may be joined to the crotchless panty 52 at different positions along the lengths of the VELCRO strips 80, 82. Thus, the friction zone 90 can be placed adjacent to the leg and side portion 62; be placed in the opposite direction and lie adjacent to the leg and thigh portion 60; or be centrally positioned directly over the aperture 64 to lie substantially in the medial plane of the body. This ability to position the friction zone 90 as needed over externalized end of the radioactive appliance (left or right as well as upwards or downwards) provides a rapid and correctable means for adjusting and, if necessary, readjusting the X and Y axis positioning of the appliance via the individual member 70 and the friction zone 90.

In addition, the individual member 70 may be fitted tighter or looser over the crotchless, rectangular-shaped aperture 64 and raised or lowered around the medial plane of the body by raising or lowering the point of attachment and closure between the aligned VELCRO strips 80, 82. The degree of fit and tightness around the crotch area of the panty provided by the single member 70 after attachment to the encircling girdle 58 optionally generates a compression force which is exerted primarily through the friction zone 90 directly onto the inserted radiotherapeutic appliance lying within the female genital organs. The quantum of compression force is increased by uplifting and tightening the individual members 70 around the crotch area; whereas the degree of compression force exerted is diminished by lowering and loosening the fit around the crotch area of the panty. In this manner, the depth of insertion for the inserted radioactive implant is maintained and controlled directly by the compression forces exerted by the individual member 70. In this manner also, the depth or Z-axis direction control for the garment is again provided by the single member 70.

It will be recognized and appreciated therefore that within this first preferred embodiment, a single member 70 is employed; that this single member alone provides the means for engaging the externalized end of the appliance and also provides the means for securing the externalized end of the appliance. This single component part thus provides the means for maintaining and securing the externalized end of the radioactive implant after it has been inserted within the female genital organ in the X-axis, in the Y-axis, and in the Z-axis concurrently. The use of a single member 70 which is attachable to and detachable from the crotchless panty comprising the supporting band in this first preferred embodiment is one of its most distinctive features and benefits. Via the use of this single member, the physician and/or attending nurse can in one motion control the entirety of the radiotherapeutic appliance via its externalized end in all three X, Y, Z axes concurrently.

Figure 8:
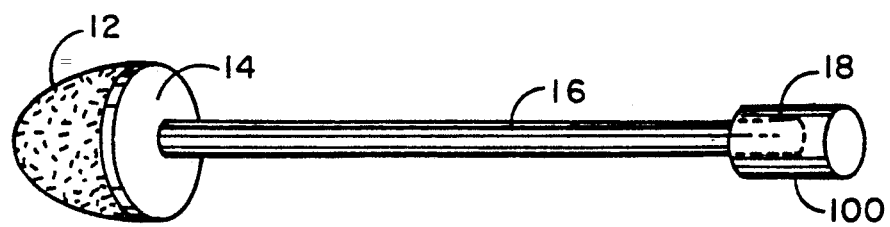
FIG. 8 is a perspective view of the engagement fitting of FIG. 7 disposed upon the radiation implant of FIG. 1.
Figure 7:
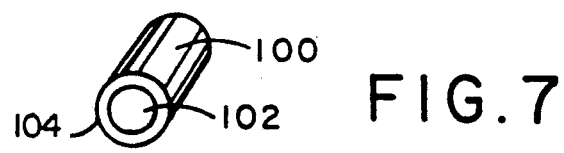
FIG. 7 is a perspective view of one type of appliance engagement fitting.

Another optional, but highly desirable, feature available for use with this first preferred embodiment is illustrated via FIGS. 7-8 respectively. FIG. 7 shows an appliance engagement fitting 100 which is intended to be fitted over and engage the externalized end of the radiotherapeutic appliance as shown within FIG. 8. The appliance engagement fitting 100 is configured as a substantially cylindrical article, having an internal void space 102 and an internal void configuration 104 which conforms to the shape and dimensions of the radiotherapeutic appliance at its end. As shown by FIG. 8, the fitting 100 is intended to engage and be inserted over the externalized end of the radiotherapeutic appliance; and provides both additional support, securing means, and a broader surface area for engagement with the single member 70 of the first preferred embodiment. As noted by FIG. 8, the particular radioactive implant illustrated is that described previously in FIG. 3; and the engagement fitting 100 is purposefully dimensioned and configured for close fitting and contact with the rod-like shaft 16 at the externalized end 18.

As noted previously herein, and as illustrated by Figs. 1-3 respectively, the radiotherapeutic appliances conventionally available appear in a variety of diverse shapes, forms, and sizes—each of which has a distinctive end which will extend externally after the majority of the radiotherapeutic appliance has been inserted internally into the female genital organs. Thus, if an appliance engagement fitting is to be employed (as is desirable in many use circumstances) it is necessary and required that the engagement fitting conform to the externalized end of the appropriate appliance as it is used in-vivo.

Moreover, the engagement fitting may optionally provide a secondary means for increasing or decreasing the degree of compression force exerted by the member 70 in the first preferred embodiment. This variance in compression force is provided by altering the size and configuration of the surface features of the fitting topographically. A representative, but nonexhaustive, showing of various engagement fittings in alternative configurations, sizes, and purpose is provided by FIGS. 9A-9F respectively. All of these alternative fittings are intended to conform to and to engage that portion of a radiotherapeutic appliance which extends from the vaginal canal after the appliance has been inserted and positioned as needed within the female genital organs; and all of these fittings are to be placed at the end of the radiotherapeutic appliance and to engage the end of that appliance firmly for a predetermined period of time and usage. Nevertheless, the fittings individually illustrated via FIGS. 9A-9F show a remarkable diversity and range of increasing and decreasing compression forces generated and exerted by the single member of the first preferred embodiment as described herein.

Figure 9E:
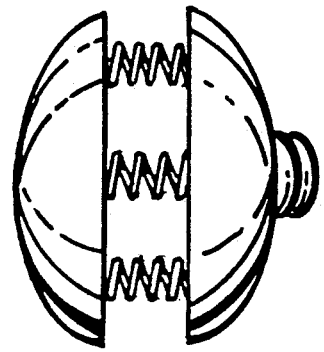
FIGS. 9A-9F are views of alternative appliance engagement fittings.
Figure 9F:
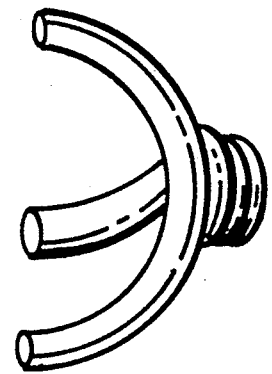
Figure 9C:
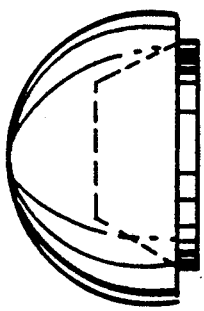
Figure 9D:
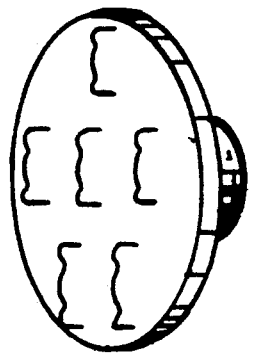
Figure 9A:
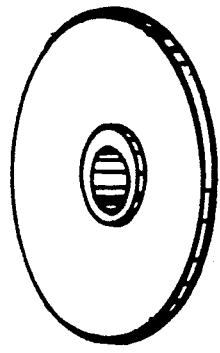
Figure 9B:

In particular, it will be noted that the individual fittings illustrated by FIGS. 9A, 9D, and 9F are intended to markedly increase the degree of compression force generated and exerted by a single member after it has been attached to the anterior aspect of the supporting band. Conversely, the fittings illustrated by FIGS. 9B, 9C and 9E will effectively diminish and reduce the amount of compression force generated and exerted by the member after it has been attached to the anterior aspect of the crotchless panty. The various configurations and styles of engagement fittings illustrated by FIG. 9, individually and collectively therefore, demonstrate the secondary means by which the surface area provided by the externalized end of the radiotherapeutic appliance may be either increased or decreased; and the degree of compression force consequently generated and exerted by the single member of the first preferred embodiment similarly increased or decreased as a consequence. As noted previously, the use of such appliance engagement fittings—regardless of configurations and dimensions—is entirely optional with the physician and/or attending nurse and the use circumstances.

B. A Second Preferred Embodiment

Figure 10:
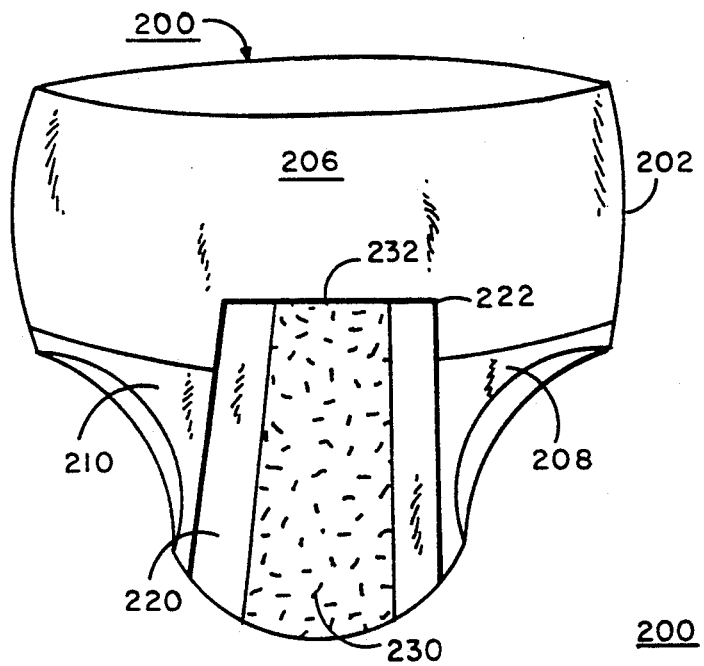
FIG. 10 is a rearward view of a second preferred embodiment of the present invention.
Figure 11:
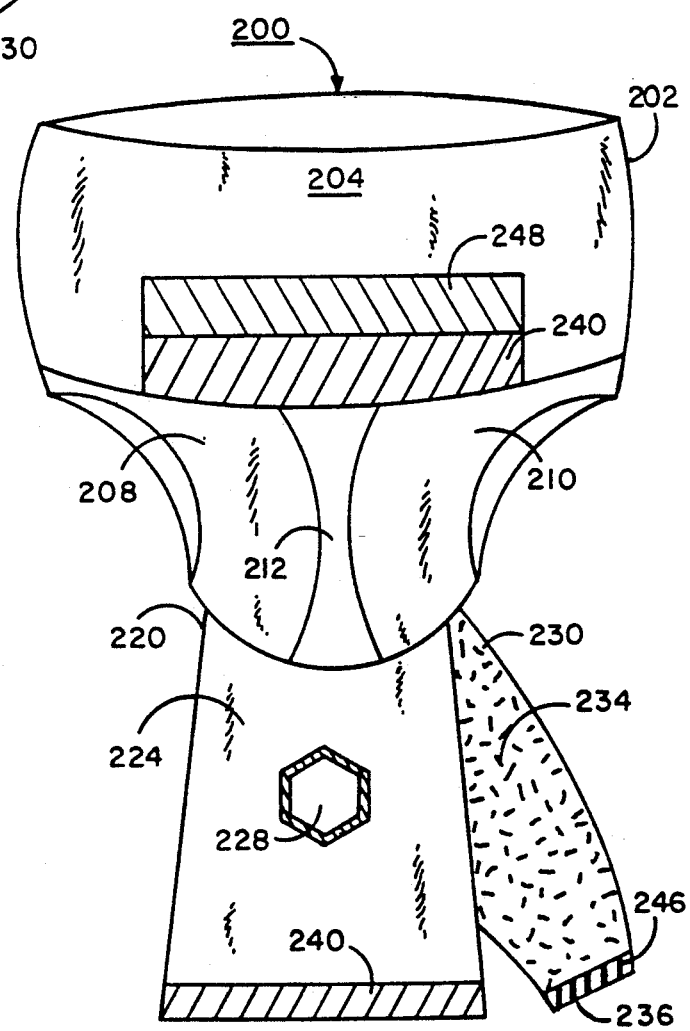
FIG. 11 is a forward view of the second preferred embodiment of FIG. 10.

A second preferred embodiment is illustrated by FIGS. 10-17 respectively. A rear view of the second preferred embodiment is illustrated by FIG. 10; and frontal views of this second preferred embodiment as employed in various modes and applications are illustrated by Figs. 11-17 individually and cumulatively. This second preferred embodiment is also a panty style garment but differs markedy from that described previously herein by employing a plurality of different members and by using a split-crotch form of access to the vulva of the patient.

As shown therein, a split-crotch panty with multiple member 200 has a supporting band formed as an encircling girdle 202 with an anterior aspect 204; a posterior aspect 206; leg and thigh section 208, 210 forming a split-crotch area; and a substantially hour-glass shaped aperture 212 which provides on demand access to the vulva of the person. A plurality of members exist within this second preferred embodiment and appears as a primary member 220 and a secondary member 230. Both the primary member 220 and the secondary member 230 are joined to the posterior aspect 206 of the encircling girdle 202 comprising the supporting band in this embodiment. The alignment and positioning of these members are revealed by FIGS. 10 and 11; and shows that the secondary member 230 lies adjacent to and disposed upon the primary member 220 in the manner illustrated.

The primary member 220 comprises a first end 222, a primary body 224, and a second end 226. The first end 222 is fixed to the posterior aspect 206 of the encircling girdle 202. The body 224 extends substantially about the medial plane of the female person and will overlay the leg and thigh sections 208, 210 of the panty. The second end 226 is attachable to and detachable from the anterior, aspect 204 of the encircling girdle 202 by virtue of VELCRO, strip 240 located on the anterior aspect 204 and by the VELCRO strip positioned at the second end 226.

This primary member 220 also comprises an optional, but highly desirable, hole 228 which is located within the body portion 224 proximal to the second end 226. This hole 228 appears within FIGS. 11-17 as a substantially hexagonal shape perforation which is reinforced along its edges to prevent shredding or accidental tearing of the fabric material. While the exact location of the hole 228 within the body section 224 may be varied in major degree, the general location will be such that the hole lies substantially within the medial plane of the body and will overlie the hour-glass shaped aperture 212 when the primary member 22 is attached to the anterior aspect 204 of the encircling girdle 202. Moreover, as appears in FIGS. 14 and 16, the primary member 220 may be attached via VELCRO strips 240, 242 in alternative directions and alignments with respect to the split-crotch area of the panty; and thus provide a means for altering the left-to-right directional positioning of the primary member 220 as it is attached to the panty itself.

Figure 12:
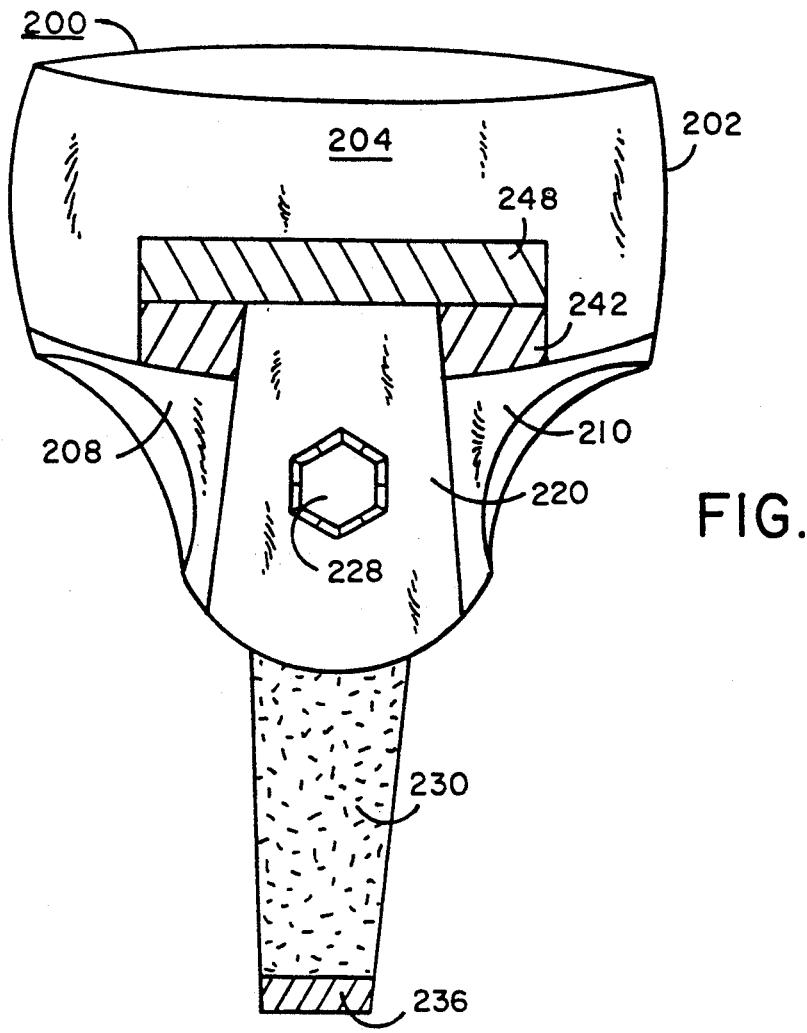
FIG. 12 is a forward view of the second preferred embodiment of FIG. 11 in a partially deployed, central alignment position.
Figure 14:
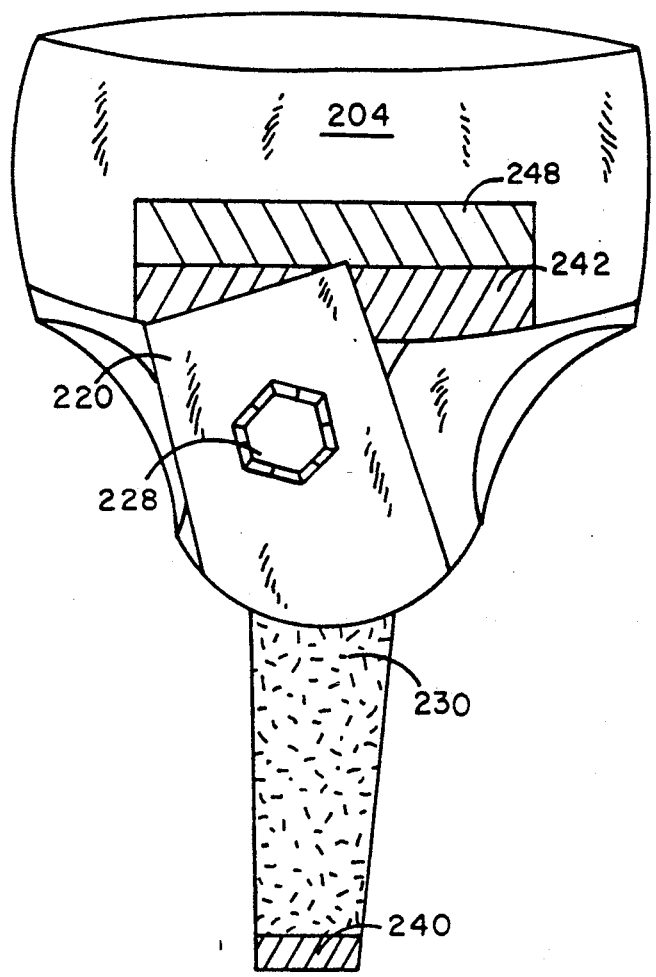
FIG. 14 is a forward view of the second preferred embodiment of FIG. 11 in a partially deployed, left alignment position.
Figure 16:
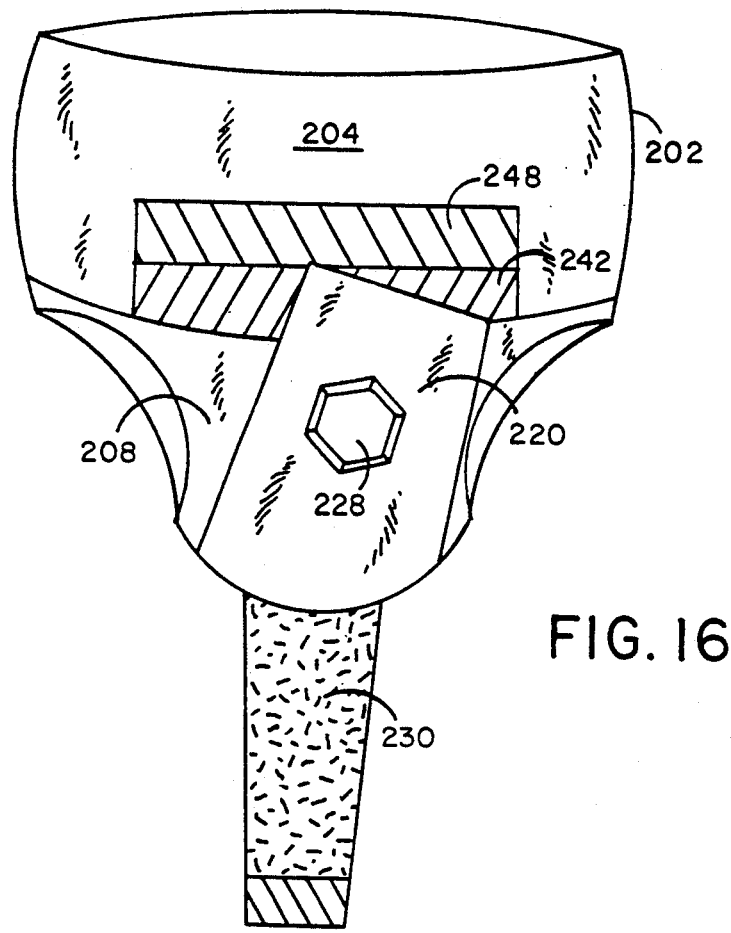
FIG. 16 is a forward view of the second preferred embodiment of FIG. 11 in a partially deployed, right alignment position.

In its intended use mode, the second preferred embodiment will be positioned on the torso of the female patient and the radiotherapeutic appliance inserted through the split crotch of the panty into the female genital organs. After the appliance has been properly positioned by the physician and/or attending nurse, the primary member is extended anteriorly such that the hole 228 encounters and passes over the externalized end of the appliance as it extends from the vaginal canal. The hole 228 thus firmly surrounds the radioactive implant or other radiotherapeutic appliance at the externalized end; and by altering the placement of the primary member when attaching it to the anterior aspect of the panty, the exact positioning of the externalized end of the appliance can be maintained and secured. This capability is illustrated by FIG. 12 when the positioning of the appliance is to be maintained substantially within the middle of the body; and is illustrated by FIG. 14 when the external end of the appliance is to be maintained somewhat left of the midline of the body; and is illustrated by FIG. 16 when the external end of the appliance is to be maintained somewhat to the right of the body's midline. Note that in each occasion, as illustrated by FIGS. 12, 14, and 16, that the positioning of the primary member 220 is maintained via the interaction of the VELCRO strips 240, 242 regardless of where the hole 228 is to be precisely located and maintained. Moreover, if the physician and/or attending nurse finds that the original closure positioning is not satisfactory for any reason whatsoever, the VELCRO strips 240, 242 may again be separated and the primary member 220 repositioned as necessary or required repeatedly in order that the proper alignment secure and maintain the position of the appliance end extending externally from the vaginal canal.

Figure 13:
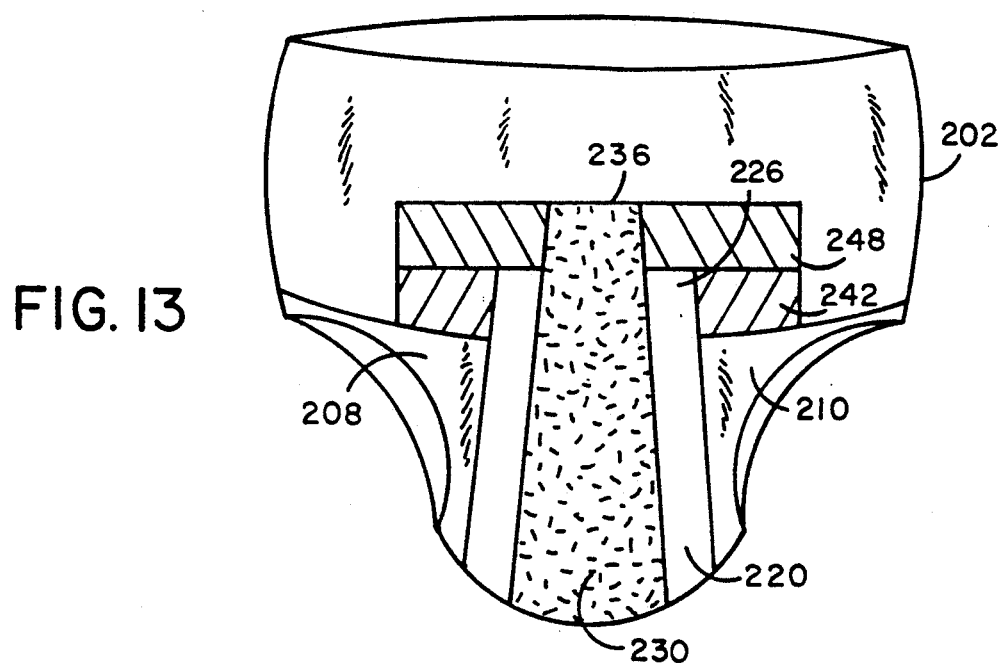
FIG. 13 is a forward view of the second preferred embodiment of FIG. 11 in a fully deployed, central alignment position.
Figure 15:
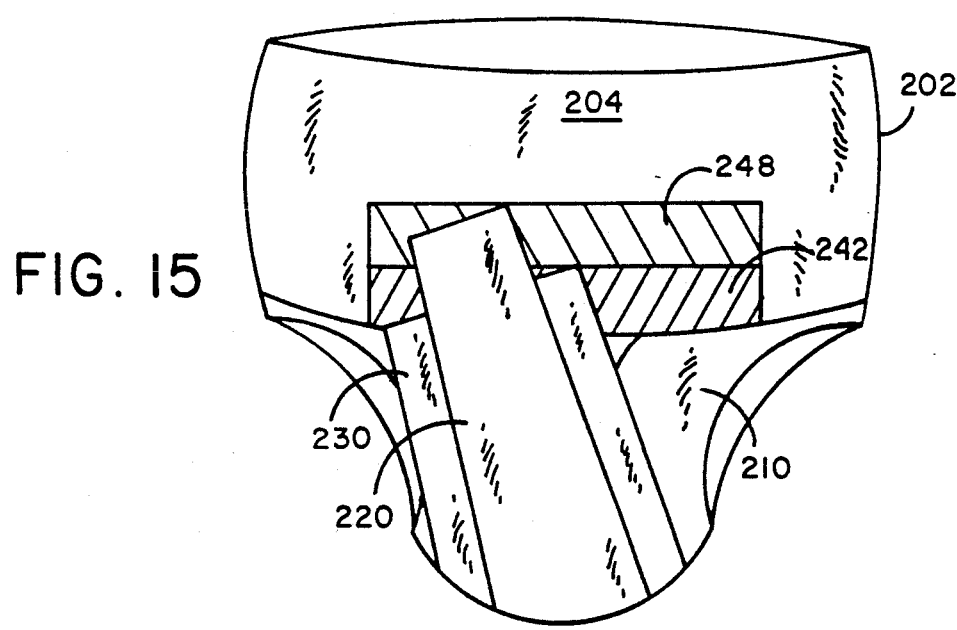
FIG. 15 is a forward view of the second preferred embodiment of FIG. 11 in a fully deployed, left alignment position.
Figure 17:
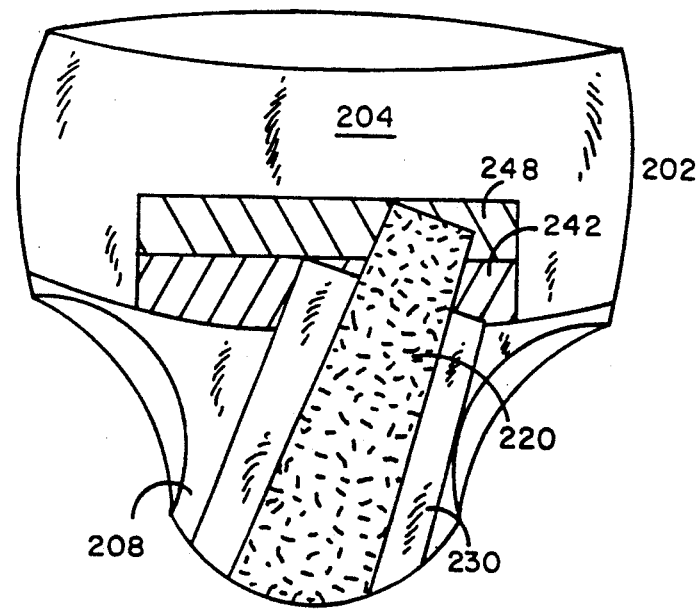
FIG. 17 is a forward view of the second preferred embodiment of FIG. 11 in a fully deployed, right alignment position.

The secondary member 230 also comprises a first end 232, a body section 234, and a second end 236. Along the second and 236 is disposed a VELCRO strip 246 intended for contact with VELCRO strip 248 on the anterior aspect 204 of the encircling girdle 202. When the secondary member 230 is extended about the medial plane of the body it will overlay both the primary member 220, the hole 228, and the end of the radiotherapeutic appliance extending externally from the vaginal canal through the hole 228. Thus, when the secondary member is properly extended and the closure made between VELCRO strips 246, 248—the externalized end of the therapeutic appliance is encountered; and a compression force generated upon appliance internalized within the female genital organs. This is illustrated by FIGS. 13, 15, and 17 respectively. The attachment of the secondary member 230 in the manner shown thereby generates and exerts a compression force directly upon the externalized end of the radiotherapeutic appliance as it lies within the vaginal canal of the person; and by controlling the tightness and fit of the secondary member, a increase or decrease in exerted compression force is generate and maintained as needed or required.

A notable feature of the second preferred embodiment is the use of the primary member 220 and the hole 228 to control and maintain the position of the therapeutic appliance as it extends externally from the vaginal canal in the X and Y axes concurrently. By changing the attachment position of the primary member 220, the X and Y coordinates of the hole 228, and consequently the external end of the inserted therapeutic appliance, may be altered once or repeatedly as necessary. Similarly, the compression force generating means is optionally provided by secondary member 230. Not only is the quantum of compression force variable and altered by tightening or loosening the placement of the secondary member 230 as it overlays the primary member 220; but the depth of the inserted radiotherapeutic appliance may be carefully controlled and maintained regardless of how many repositionings of the appliance are made in the X and Y directions. It is also highly desirable in this second preferred embodiment that the length of the extensible secondary member 230 be somewhat greater than the primary member 220 in order that the closure provided by VELCRO strips 246, 248 be made after the primary member has been positioned. Here also the degree and manner of closure is highly variable; and is intended to be individually adjusted at the moment of usage for the best positioning and comfort of the patient for local radiation therapy.

Figure 19:
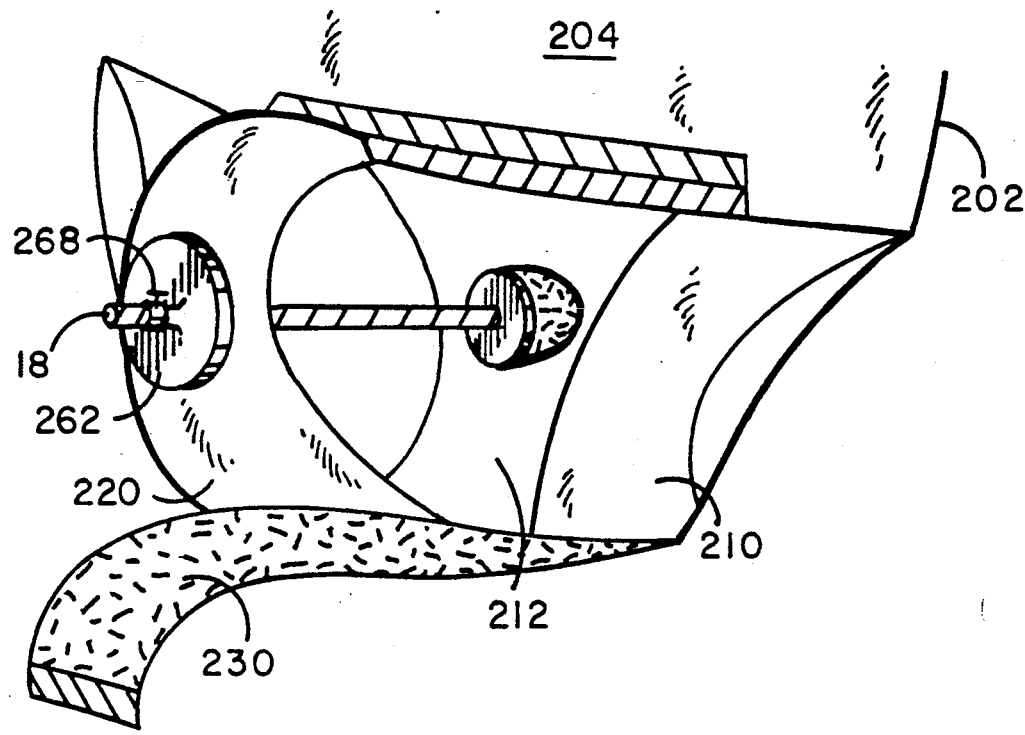
FIG. 19 is a side view of the depth controller of FIG. 18 employed in combination with the second preferred embodiment of FIG. 11.
Figure 18:
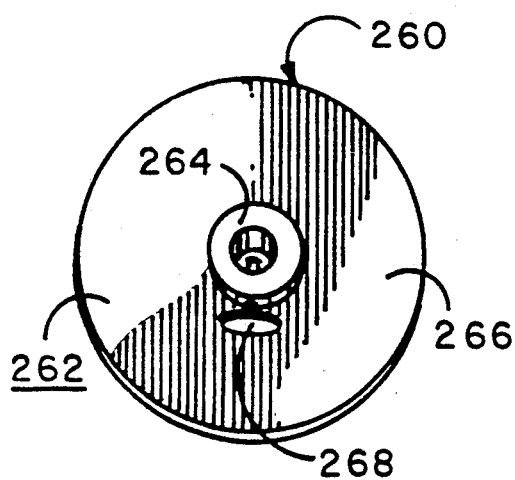
FIG. 18 is a perspective view of one type of depth controller useful with the second preferred embodiment of FIG. 11.
Figure 20E:
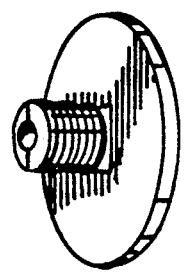
FIGS. 20A-20F are views of alternative depth controllers useful with the present invention.
Figure 20F:
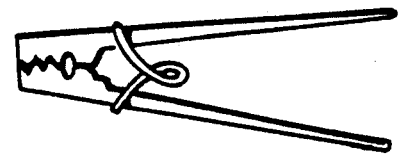
Figure 20C:
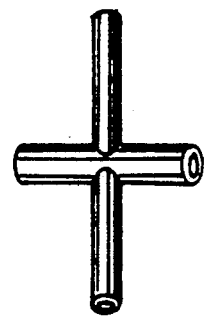
Figure 20D:
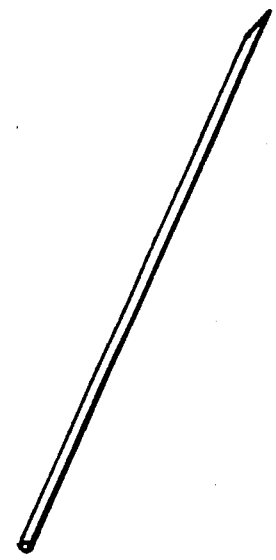
Figure 20A:
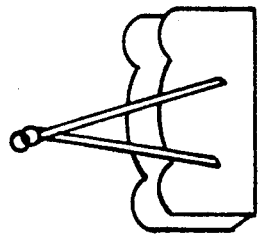
Figure 20B:
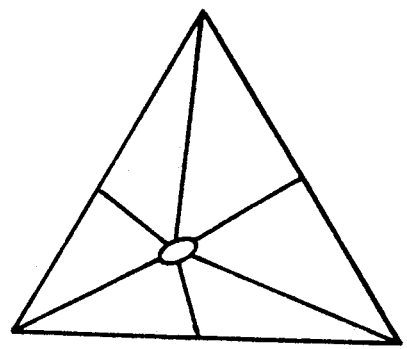

Another notable optimal feature and advantage of this second preferred embodiment is illustrated by FIGS. 18 and 19. By the very presence and intended manner of using both the primary member and the secondary member comprising the second preferred embodiment, the user may employ a depth controller 260 as a highly desirable but optional means for controlling the depth of the inserted radiotherapeutic appliance and for securing the appliance more firmly during local radiation therapy.

One embodiment of the depth controller is shown by FIG. 18 which is a substantially circular flange 262 having a shaft segment 264, and a planar segment 266, and a locking screw 268. The configuration and dimensions of the shaft segment 264 are purposefully chosen to accommodate the end of the appliance which will extend externally from the vaginal canal after the radiotherapeutic appliance has been inserted internally into the female genital organs This is illustrated by FIG. 19. It will be noted also that the radioactive implant illustrated by FIG. 19 is identical to that shown by FIG. 3; and that the circular flange 262 slides along the rod-like shaft 16 at the end 18 after the shaft has passed through the hole 228 of the primary member 220. By adjusting the distance along the shaft 16 at which the circular flange 262 is positioned, the primary member 220 becomes ever more firmly secured; and the depth to which the appliance itself has been placed within the vaginal canal becomes far more selectively controlled and firmly secured. Moreover, after the secondary member 230 has been attached to the encircling girdle 202 comprising the supporting band, the desired quantum of compression force is generated and exerted upon the externalized end of the appliance without fear of accidentally forcing the appliance deeper into the vaginal canal and/or thus forcing an unwanted dislocation and loss of correct positioning for the radiotherapeutic appliance itself. Thus, by loosening the locking screw 268, the flange 262 may be slid along the shaft 16 of the implant at any distance backwards and forwards as necessary and desirable until a precise location is chosen by the attending physician or nurse. Then the locking screw is tightened and the flange will remain immobilized at the chosen location. In consequence and result thereof, the flange provides a means for controlling and maintaining the depth of the radioactive implant after it has been inserted internally such that no further repositioning in depth will occur to any meaningful extent.

The only feature common to all configurations and styles of depth controllers as a class therefore is that each controller be individually adjustable along the shaft or length of the radiotherapeutic appliance with which it is intended to be employed. Thus, any means which conforms to the shape or dimension of the particular appliance employed is suitable; and a wide variety of such depth controllers are possible and envisioned—as are represented by FIGS. 20A–20F respectively.

It will be noted that the only common feature among the depth controllers of FIG. 20 is that each is intended to reside upon the shaft or length of the implant or other appliance along the end extending externally from the vaginal canal; and that the particular means of attachment, dislodgement, and repositioning will vary with each embodiment and style. Thus, a spring clamp is shown by FIG. 20A which can be located and repositioned if necessary at will. Similarly, the friction bearing retainer of FIG. 20B must encompass the circumference of the shaft or cylinder of the appliance and relies upon a mode of friction for lodgement and displacement as needed. The format illustrated by FIG. 20C is intended as a screw thread arrangement which advances and recedes along a cylinder or rod-like shaft as necessary. The embodiment of FIG. 20D is a surgical needle which is intended to penetrate the substance of the appliance itself through its thickness and thus secure the depth of the appliance in a manner similar to that employed by a cotter pin. The format shown by FIG. 20E is generally a rubber or elastomeric article which slides along the shaft perimeter of the appliance and relies upon friction to maintain the controller at the proper distance. Finally, the clothes pin clamp of FIG. 20F is conventionally known and may be easily attached and detached as necessary to provide proper positioning, securement, and alignment. All of the various depth controllers illustrated by FIG. 20 are merely representative of the diverse range possible; and all of these may be usefully employed as auxiliary means by which to control the depth and degree of securement for the radiotherapeutic appliance after it has been inserted internally.

C. The Third Preferred Embodiment

A preferred third embodiment of the invention is illustrated by FIGS. 21-24 respectively. These figures show all the essential component parts as well as the mode of intended usage which follows in principle and practice the pattern previously described for the first and second preferred embodiments respectively herein. As shown by FIGS. 21-24, the third preferred embodiment is also a panty style garment which includes a supporting band configured as a panty having an open, triangular-shaped, crotch area. The supporting band comprises an encircling girdle 302 having an anterior aspect 304 and a posterior aspect 306 (not shown). The supporting band also comprises thigh and leg sections 308, 310 and a triangular-shaped aperture 312 in the crotch area of the panty.

After the garment has been positioned on the torso of the person, the radiotherapeutic appliance is to be inserted into the female genital organs via the triangular-shaped aperture 312. As shown in FIGS. 21-24, the radioactive implant of FIG. 1 is employed illustratively for this purpose.

Figure 22:
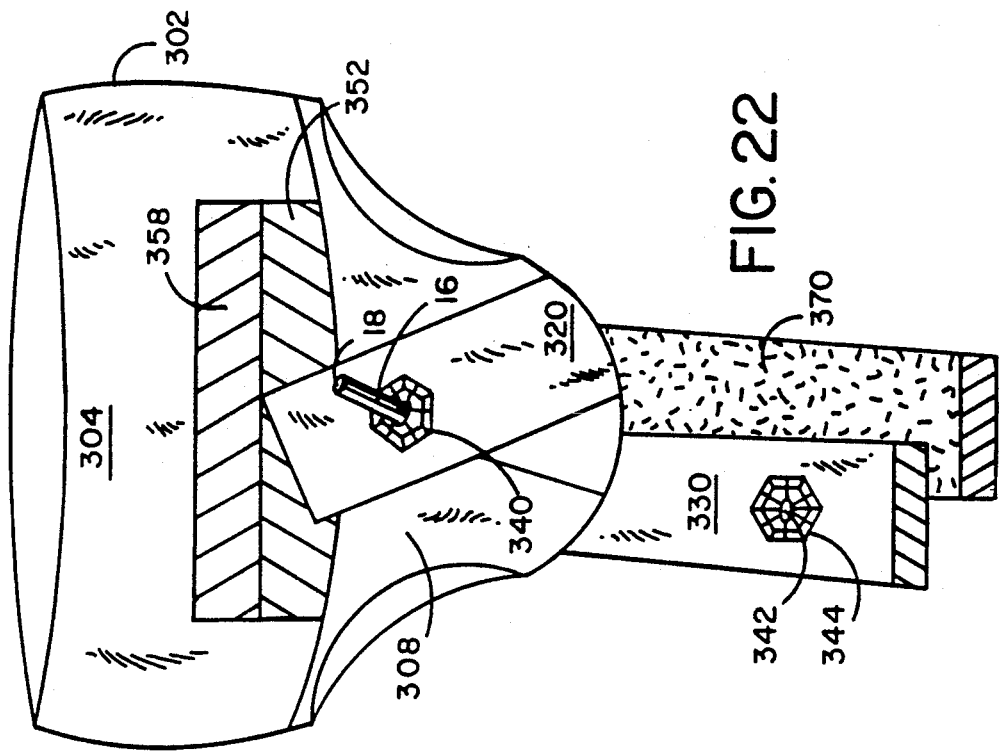
FIG. 22 is a frontal view of the third preferred embodiment of FIG. 21 in an initial partially deployed stage.
Figure 21:
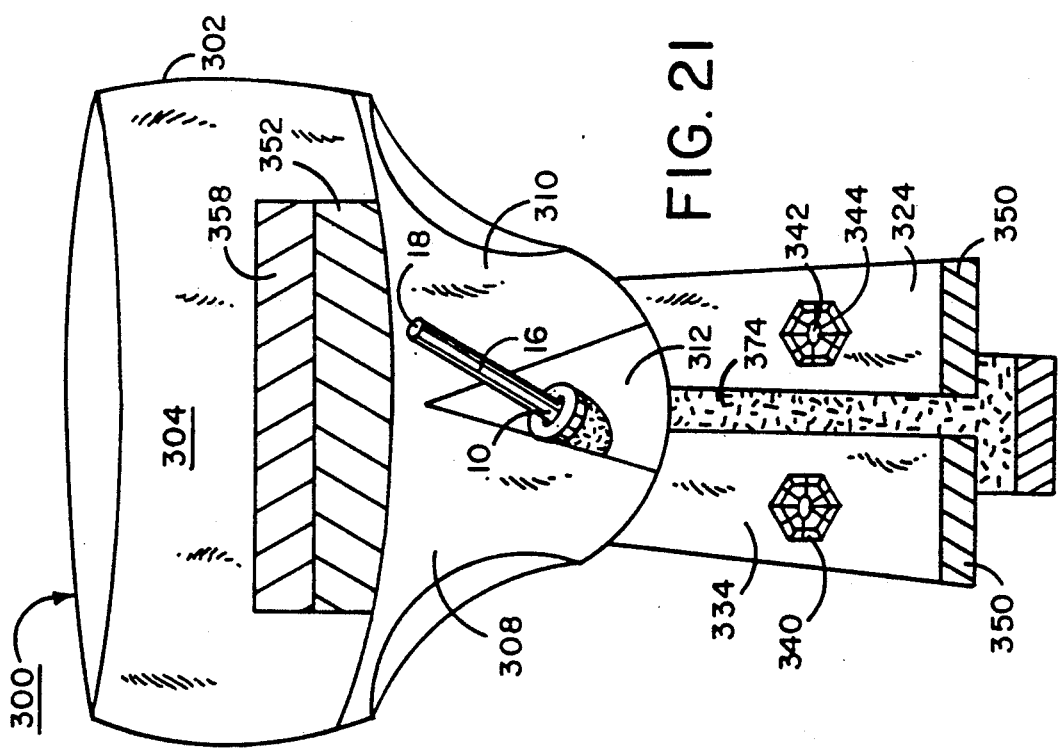
FIG. 21 is a frontal view of a third preferred embodiment of the present invention.
Figure 23:
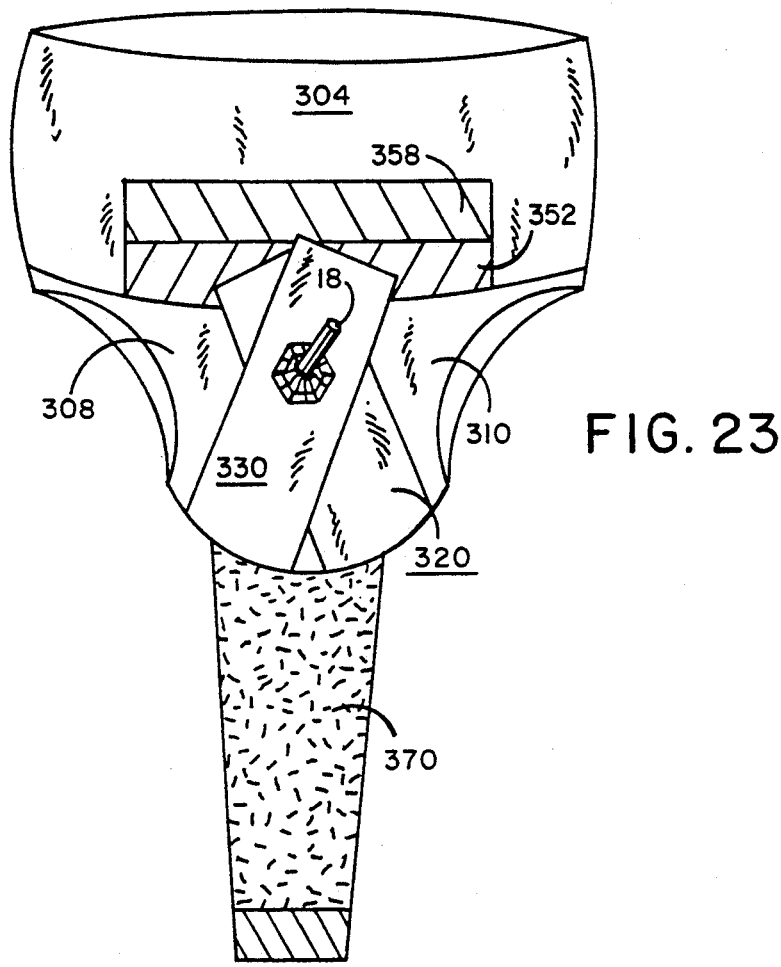
FIG. 23 is a frontal view of the third preferred embodiment of FIG. 21 in a follow-up partially deployed stage.

This third embodiment is unique in that it employs two different members for positioning the externalized end of the radioactive implant, one planar member each being used for the X-axis orientation and a different member being used to position the appliance in the Y-axis orientation. These appear as first positioning member 320 and second positioning member 330 respectively. The first positioning member 320 comprises a first end attached to the posterior aspect 306 of the encircling girdle 302, a body section 324, and a second end 326. Similarly, the second positioning member 330 has a first end 332 fixed to the posterior aspect of the encircling girdle, a body section 334, and a second end 336. As shown by FIGS. 22 and 23, within the body sections 324, 334 of each positioning member, there appear a positioning aid 340 having a central hole 342 and a plurality of friction edges 344. As each positioning member 320, 330 is extended substantially about the medial plane of the body and as each overlaps the triangular-shaped aperture 312 of the panty, the external end 18 of the inserted radioactive implant (which extends externally from the vaginal canal) passes through each positioning aid 340 individually via its central hole 342; and the shaft 16 of the radioactive implant is held firmly in adjustable position along its length via friction edges 344 of each positioning aid 340 individually. The positioning aids 340 on the first and second positioning members 320, 330 may be moved and adjusted up and down the length of the externalized shaft end in order to more selectively secure and control the position of the implant as it lies internally within the female genital organs. Each of the positioning members 320, 330 has a VELCRO strip 350 proximal to the ends 326, 336; and each VELCRO strip 350 individually will engage and join with the corresponding VELCRO strip 352 located on the encircling girdle 302. Thus, as the first positioning member 230 overlays the vulva of the person, the positioning aid 340 encompasses the externalized end of the radiotherapeutic appliance and closure is made between the VELCRO strips 350 and 352—resulting in a firm positioning of the appliance in the X-axis, as shown by FIG. 22. Subsequently, the second positioning member is extended about the medial plane of the body to also overlay the vulva such that the externalized end of the appliance fits through the positioning aid 340; and becomes aligned thereby in the Y-axis orientation by attaching the second positioning member 330 via VELCRO strips 350, 352 as illustrated by FIG. 23. In this manner, the radiotherapeutic appliance is maintained and secured in proper and correct position by the overlapped first and second positioning members.

Figure 24:
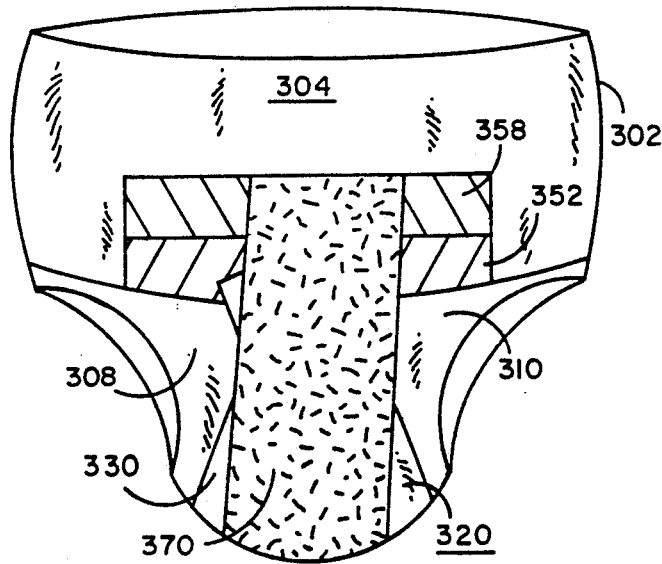
FIG. 24 is a frontal view of the third preferred embodiment of FIG. 21 is a fully deployed stage.

The third member 370 functions as a compression force generating member; and comprises a first end 372, a body section 374, and a second end 376. As in other embodiments, the first end is joined to the encircling girdle along its posterior aspect; the body section is extensible along the medial plane of the body anteriorly and will overlay the vulva of the person; and the second end 37 is attachable to and detachable from the anterior aspect of the encircling girdle. This force generating member 370 is generally longer in length than the positioning members 320, 330; and slows attachment and detachment repeatedly as needed after the positioning members have been properly placed. A VELCRO strip 356 lies proximal to the second end 376 and is aligned for attachment to the VELCRO strip 358 on the anterior aspect of the encircling girdle comprising the supporting band of the garment. Accordingly, following the previously described manipulations, the force generating member 370 overlays the positioning members and generates a compression force on the end of the radiotherapeutic appliance which extends externally from the vaginal canal. This result is illustrated by FIG. 24. Similarly, by either tightening or loosening the degree of tension provided by the member 370, a greater or lesser compression force is generated and exerted—a force which may be varied as needed or desired by the attending physician or nurse.

III. Alternative Embodiments of the Present Invention

Figure 25:
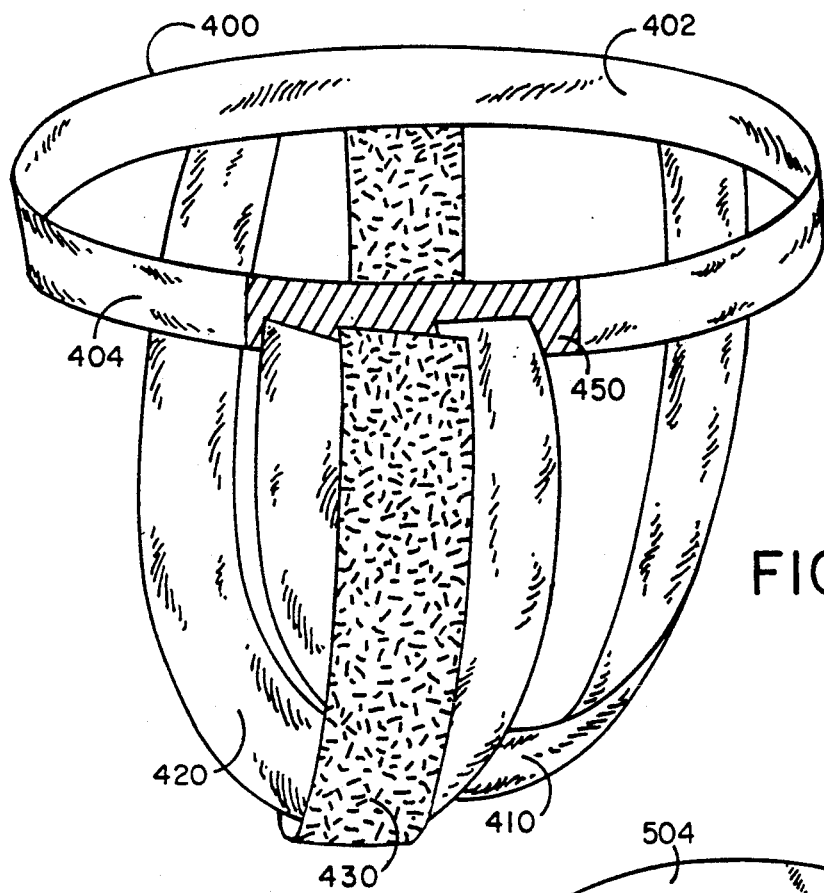
FIG. 25 is a perspective view of a first alternative embodiment of the present invention.

One alternative embodiment is illustrated by FIG. 25 and is a garment to be worn around the torso of the female body comprising a supporting band 400 and three different extensible members 410, 420, 430. The supporting band has a posterior aspect 402 and an anterior aspect 404 upon which a VELCRO strip 450 is disposed. Each of the members 410, 420, 430 is joined at one end to the posterior aspect 402; and each is individually attachable to and detachable from the anterior aspect 404 of the supporting band 400 via VELCRO strip 450. All of the members 410, 420, 430 are alike. Each member is desirably formed of flexible material; is extendable individually substantially about the medial plane of the female body; and will overlay the vulva at least in part as a consequence of its attachment to the supporting band. Moreover, there is no precise orientation or ordering as to which of the three different members overlays the other in sequence. Thus, any one of the members can provide positioning control in the X-axis direction; any second member can provide positioning control in the Y-axis direction; and the remaining third member will provide positioning control in the Z-axis orientation.

It will be appreciated also that the appliance engagement fitting illustrated by FIGS. 7 and 8 are equally suitable for use in this alternative embodiment as well. In addition, any one or more of the individual members 410, 420, 430 may have one or more perforations within its body and thus permit the externalized end of the appliance to pass therethrough in the manner previously described herein. In such instances, the depth controllers illustrated by FIGS. 18 and 19 may be usefully employed with this embodiment as well.

Another alternative embodiment of the present invention is shown by FIG. 26. This alternative embodiment is probably the least desirable design and construction for general use; but may be suitable for extraordinary use circumstances where the patient cannot endure constriction or pressure around the abdomen and waist. Accordingly, the garment 500 as shown includes two individual side loops 502; an enveloping sash 504; and an inner thigh section 506. Centrally located within the inner thigh section 506 is a cutout 508 which substantially encircles and encompasses the vulva of the patient and provides on-demand access to the female genital organs. Lying along the perimeter of the cutout 508 on the inner thigh section 506 is a VELCRO strip 510 or other closure means.

A single extensible member 520 is present as a component part in this alternative embodiment; and this member comprises a first end 522 joined to the enveloping sash 504 at its posterior aspect; a body section 524 which is extensible substantially about the medial plane of the patient to overlay the vulva of the patient; and a second end 526 which is attachable to and detachable from the inner thigh section 506 along the cutout 508 via the VELCRO strip 510.

In these alternative embodiments, each embodiment of the present invention is first positioned around the torso of the female body such that the supporting band supplies access on demand to the vulva of the person. A suitable radiotherapeutic appliance is then inserted internally into the vaginal canal and positioned as required by the attending physician or nurse. The single member or members are then extended around the buttocks of the person and pulled forward over the anterior aspects to overlay the vulva and engage the end of the radiotherapeutic appliance extending externally from the vaginal canal. As the member or members are individually attached to the supporting band along the anterior aspect, a compression force is then generated and exerted upon the externalized end of the inserted appliance; and the entirety of the radiotherapeutic appliance is maintained in position and secured against accidental dislodgement or other movements.

The present invention is not to be restricted in form nor limited in scope except by the claims appended hereto.

What I claim is:

1. A method for securing and maintaining the chosen position of a radiotherapeutic appliance internally after insertion within the female genital organs during local radiation therapy, said method comprising the steps of:

placing a garment externally around the lower abdomen and pelvis on the female person prior to beginning local radiation therapy, said garment comprising at least one supporting band of material having anterior and posterior aspects which are configured to be worn around the lower abdomen and pelvis of the female body without substantially covering other areas of the female body, and at least one member for securing and maintaining the chosen position of the inserted radiotherapeutic appliance within the female genital organs, said member being comprised of (1) a first end joined to said posterior aspect of said supporting band, (2) a member body extensible substantially about the medial plane of the female person to overlay the vulva at least in part, (3) a second end attachable to and detachable from said anterior aspect of said supporting band on-demand, and (4) appliance engaging means for on-demand engagement of the radiotherapeutic appliance at a chosen position after insertion internally within the female genital organs;

inserting the radiotherapeutic appliance internally within the female genital organs at a chosen position;

extending said member of said garment about the medial plane of the female person such that the vulva is overlayed at least in part by said member body and said appliance engaging means engage the inserted radiotherapeutic appliance at the chosen position within the female genital organs; and attaching said second end of said extended member to said anterior aspect of said supporting band to secure and maintain the inserted radiotherapeutic appliance internally at the chosen position within the female genital organs.

2. A method for securing and maintaining the chose position of a radiotherapeutic appliance internally after insertion within the female genital organs during local radiation therapy, said method comprising the steps of:

placing a garment externally around the lower abdomen and pelvis on the female person prior to beginning local radiation therapy, said garment comprising at least one supporting band of material having anterior and posterior aspects which are configured to be worn around the lower abdomen and pelvis of the female body without substantially covering other areas of the female body, said supporting band providing access on-demand to the vulva of the female person.

a plurality of members employed individually for securing and maintaining the chosen position of the inserted radiotherapeutic appliance within the female genital organs, each of said members being comprised of
(1) a first end joined to said posterior aspect of said supporting band,
(2) a member body extensible substantially about the medial plane of the female person to overlay the vulva at least in part,
(3) a second end attachable to and detachable from said anterior aspect of said supporting band on-demand, and
appliance engaging means upon at least one of said members for on-demand engagement of the radiotherapeutic appliance at a chosen position after insertion internally within the female genital organs;
inserting the radiotherapeutic appliance internally within the female genital organs at a chosen position;
extending said member of said garment about the medial plane of the female person such that the vulva is overlayed at least in part by said member body and said appliance engaging means engage the inserted radiotherapeutic appliance at the chosen position within the female genital organs; and
attaching said second end of said extended member to said anterior aspect of said supporting band to secure and maintain the inserted radiotherapeutic appliance internally at the chosen position within the female genital organs.

3. The method as recited in claim 1 or 2 wherein said member further comprises force generating means for exerting a compression force upon the inserted radiotherapeutic appliance to maintain the appliance internally within the female genital organs.

4. The method as recited in claim 2 wherein at least one of said members further comprises force generating means for exerting a compression force upon the inserted radiotherapeutic appliance to secure the appliance internally within the female genital organs.

5. The method as recited in claim 1 or 2 further comprising closure means situated on said anterior aspect of said supporting band.

6. The method as recited in claim 1 or 2 further comprising closure means situated upon said second end of said member.

* * * * *